(12) United States Patent
Reeder et al.

(10) Patent No.: US 9,943,246 B2
(45) Date of Patent: Apr. 17, 2018

(54) SYSTEM AND METHOD FOR ASSESSING SUSCEPTIBILITY OF TISSUE USING MAGNETIC RESONANCE IMAGING

(71) Applicant: Wisconsin Alumni Research Foundation, Madison, WI (US)

(72) Inventors: Scott B. Reeder, Middleton, WI (US); Diego Hernando, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 725 days.

(21) Appl. No.: 13/684,000

(22) Filed: Nov. 21, 2012

(65) Prior Publication Data

US 2014/0142417 A1    May 22, 2014

(51) Int. Cl.
| | | |
|---|---|---|
| *A61B 5/05* | (2006.01) | |
| *A61B 5/055* | (2006.01) | |
| *G01R 33/48* | (2006.01) | |
| *A61B 5/00* | (2006.01) | |

(52) U.S. Cl.
CPC ............ *A61B 5/055* (2013.01); *A61B 5/4244* (2013.01); *G01R 33/4828* (2013.01); *A61B 5/004* (2013.01)

(58) Field of Classification Search
None
See application file for complete search history.

(56) References Cited

U.S. PATENT DOCUMENTS

| | | | |
|---|---|---|---|
| 2007/0247153 A1* | 10/2007 | Yu et al. ................. | 324/307 |
| 2011/0044524 A1* | 2/2011 | Wang .................... | G01R 33/54 382/131 |

OTHER PUBLICATIONS

Liu et al. Calculation of Susceptibility Through Magnetic Orientation Sampling (COSMOS): A Method for Conditioning the Inverse Problem From Measured Magnetic Field Map to Susceptibilitiy Source Image in MRI. Magnetic Resonance in Medicine. 61:196-204. 2009.*
Sirllin et al., "Magnetic Resonance Imaging Quantification of Liver Iron", Magn Reson Imaging, Aug. 2010.*
Yu et al., "Multi-Echo Water-Fat Separation and Simultaneous R2* Estimation with Multi-Frequency Fat Spectrum Modeling", Magn Reson Med., Nov 2008.*
de Rochefort et al., "Quantitative MR Susceptibility Mapping Using Piece-Wise Constant Regularized Inversion of the Magnetic Field", Mag. Reson. in Med., 2008.*
Bilgic et al., "MRI estimates of brain iron concentration in normal aging using quantitative susceptibility mapping", NeuroImage 59, 2012, available online Sep. 7, 2011.*
Bydder, et al., Relaxation Effects in the Quantification of Fat Using Gradient Echo Imaging, Magn. Reson. Imaging, 2008, 26(3):347-359.
Chu, et al., MRI Measurement of Magnetic Susceptibility Using Volumetric Breath-Hold Gradient Echo Technique: A Phantom Study, Proc. Intl. Soc. Mag. Reson. Med., 2003, 11, p. 998.
Chu, et al., MRI Measurement of Hepatic Magnetic Susceptibility—Phantom Validation and Normal Subject Studies, Magnetic Resonance in Medicine, 2004, 52:1318-1327.

(Continued)

*Primary Examiner* — Christopher Cook
(74) *Attorney, Agent, or Firm* — Quarles & Brady LLP

(57) ABSTRACT

A system and method for assessing magnetic susceptibility of tissue of a subject using a magnetic resonance imaging (MRI) system to acquire chemical-shift-encoded, water-fat separated data. From the water-fat separated data, separated water and fat images, as well as a magnetic field inhomogeneity map are used to estimate the magnetic susceptibility within tissue.

20 Claims, 5 Drawing Sheets

(56) References Cited

OTHER PUBLICATIONS

De Rochefort, et al., Quantitative MR Susceptibility Mapping Using Piece-Wise Constant Regularized Inversion of the Magnetic Field, Magnetic Resonance in Medicine, 2008, 60(4):1003-1009.
Deville, et al., NMR Multiple Echoes Observed in Solid 3He, Physical Review B, 1979, 19:5666-5688.
Hernando, et al., Joint Estimation of Water/Fat Images and Field Inhomogeneity Map, Magnetic Resonance in Medicine, 2008, 59:571-580.
Hernando, et al., Robust Water/Fat Separation in the Presence of Large Field Inhomogeneities Using a Graph Cut Algorithm, Magnetic Resonance in Medicine, 2010, 63:79-90.
Hernando, et al., Chemical Shift-Based Water/Fat Separation: A Comparison of Signal Models, Magnetic Resonance in Medicine, 2010, 64(3):811-822.
Hernando, et al., Addressing Phase Errors in Fat-Water Imaging Using a Mixed Magnitude/Complex Fitting Method, Magnetic Resonance in Medicine, 2012, 67(3):638-644.
Hernando, et al., R2* Mapping in the Presence of Macroscopic B0 Field Variations, Magnetic Resonance in Medicine, 2012, 68(3):830-840.
Koch, et al., Rapid Calculations of Susceptibility-Induced Magnetostatic Field Perturbations for In Vivo Magnetic Resonance, Physics in Medicine and Biology, 2006, 51(24):6381-6402.
Li, et al., Quantitative Susceptibility Mapping of Human Brain Reflects Spatial Variation in Tissue Composition, NeuroImage, 2011, 55(4):1645-1656.
Liu, et al., Fat Quantification with IDEAL Gradient Echo Imaging: Correction of Bias from T1 and Noise, Magnetic Resonance in Medicine, 2007, 58:354-364.
Liu, et al., High-Field (9.4 T) MRI of Brain Dysmyelination by Quantitative Mapping of Magnetic Susceptibility, NeuroImage, 2011, 56(3):930-938.
Liu, et al., Unambiguous Identification of Superparamagnetic Iron Oxide (SPIO) Particles Through Quantitative Susceptibility Mapping of the Nonlinear Response to Magnetic Fields, Magn. Reson. Imaging, 2010, 28(9):1383-1389.
Longo, et al., Proton MR Spectroscopy in Quantitative In Vivo Determination of Fat Content in Human Liver Steatosis, Journal of Magnetic Resonance Imaging, 1995, 5(3):281-285.
Poonawalla, et al., Adipose Tissue MRI for Quantitative Measurement of Central Obesity, Journal of Magnetic Resonance Imaging, 2013, 37(3):707-716.
Reeder, et al., Multicoil Dixon Chemical Species Separation With an Iterative Least-Squares Estimation Method, Magnetic Resonance in Medicine, 2004, 51:35-45.
Reeder, et al., On the Definition of Fat-Fraction for In Vivo Fat Quantification with Magnetic Resonance Imaging, Proc. Intl. Soc. Mag. Reson. Med., 2009, 17, p. 211.
Reeder, et al., Relationship Between Proton-Density Fat-Fraction and True Fat Concentration for In Vivo Fat Quantification with Magnetic Resonance Imaging, Proc. Intl. Soc. Mag. Reson. Med., 2011, 19, p. 805.
Schweser, et al., Quantitative Imaging of Intrinsic Magnetic Tissue Properties Using MRI Signal Phase: An Approach to In Vivo Brain Iron Metabolism?, NeuroImage, 2011, 54(4):2789-2807.
Taylor, et al., Simultaneous Field and R*2 Mapping to Quantify Liver Iron Content Using Autoregressive Moving Average Modeling, Journal of Magnetic Resonance Imaging, 2012, 35:1125-1132.
Vasanawala, et al., Estimation of Liver T*2 in Transfusion-Related Iron Overload in Patients with Weighted Least Squares T*2 IDEAL, Magnetic Resonance in Medicine, 2012, 67(1):183-190.
Wang, et al., Magnetic Resonance Imaging Measurement of Volume Magnetic Susceptibility using a Boundary Condition, Journal of Magnetic Resonance, 1999, 140:477-481.
Wang, et al., Quantification of the Magnetic Susceptibility of the Heart Using MRI: Demonstration on Normal Subjects, Proc. Intl. Soc. Mag. Reson. Med., 2005, 13, p. 1666.
Wang, et al., Assessment of Cardiac Iron by MRI Susceptometry and R2* in Patients with Thalassemia, Magn. Reson. Imaging, 2010, 28(3):363-371.
Yu, et al., Multiecho Reconstruction for Simultaneous Water-Fat Decomposition and T2* Estimation, Journal of Magnetic Resonance Imaging, 2007, 26:1153-1161.
Yu, et al., Multiecho Water-Fat Separation and Simultaneous R*2 Estimation with Multifrequency Fat Spectrum Modeling, Magnetic Resonance in Medicine, 2008, 60:1122-1134.
Yu, et al., Combination of Complex-Based and Magnitude-Based Multiecho Water-Fat Separation for Accurate Quantification of Fat-Fraction, Magnetic Resonance in Medicine, 2011, 66:199-206.

\* cited by examiner

SYSTEM AND METHOD FOR ASSESSING SUSCEPTIBILITY OF TISSUE USING MAGNETIC RESONANCE IMAGING

STATEMENT REGARDING FEDERALLY SPONSORED RESEARCH

This invention was made with government support under DK083380, DK088925, and EB010384 awarded by the National Institutes of Health. The government has certain rights in the invention.

BACKGROUND OF THE INVENTION

The present invention relates, generally, to systems and methods for magnetic resonance imaging (MRI) and, more particularly, to systems and methods for measuring and quantifying substances in a subject using magnetic susceptibility.

Iron is an essential nutrient for the human body, needed by every human cell. However, excessive iron is toxic, and the body has very limited capabilities to eliminate abnormal accumulation of iron. There are a variety of conditions that afflict patients that require regular blood transfusions. For example, hese patients are at risk of developing "transfusional" iron overload. Iron overload can result in multiple complications, such as preventing normal growth and sexual maturation, and damaging the liver and heart. Treatment for transfusional iron overload is based on administering iron-reducing "chelator" agents (chemicals that bind to excess iron and remove it from the body), either orally or intravenously. Treatment with chelators is extremely expensive (>$40,000/year) and is potentially toxic. Therefore, accurate measurement of body iron levels is critical to determine when to initiate treatment. It is also important to monitor treatment (allowing the adjustment of chelator dose to maintain low iron levels while minimizing risks from the treatment).

The simplest method available to assess body iron is based on measuring serum ferritin or serum transferring receptor concentration from a blood sample. Unfortunately, it is well known that serum biochemical tests are often confounded by a number of factors and do not accurately reflect body iron levels. Hepatic iron content (HIC) is widely considered the best reference for assessing total body iron stores, because the amount of iron in the liver is closely correlated to total body iron. Currently, chemical analysis of liver biopsy samples is the best available reference standard to measure HIC. However, biopsy is limited because it is invasive, expensive ($1500-2000), and has poor sampling variability. In addition, biopsy cannot be performed in patients who have low platelets or low coagulation factors (e.g., myelodysplastic syndrome), due to the risk of uncontrolled bleeding.

Liver iron susceptometry using a superconducting quantum interference device (SQUID) is generally regarded as the most accurate non-invasive method to quantify liver iron. SQUID is a well-validated non-invasive reference standard for measuring HIC. Importantly, SQUID directly measures tissue susceptibility, which is a fundamental property of all substances including tissue. Further, the relationship between susceptibility and tissue iron concentration is well understood. This relationship is well understood because iron is the only naturally occurring non-trace substance in the body with significant magnetic susceptibility, and increases in local tissue susceptibility only occur from tissue iron overload. This fact, and direct relationship between magnetic susceptibility and iron concentration makes this a highly attractive and fundamental quantitative biomarker of tissue iron overload. Unfortunately, even though SQUID has been calibrated, validated and used for clinical studies, its complexity, high cost and limited availability (only four SQUID devices are available world-wide for this purpose) have precluded its widespread use.

Magnetic Resonance Imaging (MRI) is a widely available and accessible technology that has been shown to be very sensitive to the presence of iron. When a substance, such as human tissue, is subjected to a sufficiently-large, uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

To do so, the signals are often weighted in different ways to give preference to or consider different sub-signals or so-called contrast mechanisms. Two basic "contrast mechanisms" commonly utilized in MR imaging are the spin-lattice (or longitudinal or $T_1$) relaxation time or spin-spin (or transverse or $T_2$) relaxation time. However, there are a variety of other mechanisms for eliciting contrast in MRI, including $R_2^*$. Specifically, $T_2^*$ is a quantity related to $T_2$, but including dephasing effects. That is, $T_2^*$ is a quantity related to spin-spin relaxation and, in addition, relating magnetic field inhomogeneities and susceptibility effects. Often, instead of $T_2^*$, these quantities are preferably expressed in terms of relaxation, or the inverse of the $T_2^*$ time constant, represented as $R_2^*$.

Iron introduces microscopic inhomogeneities in the magnetic field, resulting in an increased rate of signal decay, measured by two MRI relaxation constants $R_2$ and $R_2^*$. MRI-based iron quantification methods are based on either $R_2$ or $R_2^*$ relaxivity, using spin-echo or gradient-echo sequences, respectively.

An $R_2$ method (commercially termed "Ferriscan") has been shown to provide accurate measurements of HIC and is FDA approved. This approach is based on a monotonic, curvilinear empirical calibration curve linking $R_2$ and HIC. However, Ferriscan has several important limitations that have severely curtailed its widespread use: 1) it is expensive ($300/patient, in addition to all other MRI related costs), 2) it is very slow (10-20 minutes of scanning in order to obtain adequate R2 measurements), and 3) may have limited dynamic range due to a nonlinear relationship of $R_2$ with HIC. Additionally, Ferriscan results cannot be obtained immediately after the MRI scan, but require uploading the acquired images to Resonance Health (located in Claremont, Australia), and the HIC estimate is received within two business days.

$R_2^*$-based methods have the potential to overcome these limitations. Due to the high speed of gradient-echo pulse sequences, single breath-hold whole-liver $R_2^*$ mapping is possible. In recent years, a linear relationship between R2* and HIC has been demonstrated. Further, it has been demonstrated that $R_2^*$-based methods can be confounded by several factors including the presence of fat, macroscopic susceptibility and magnitude based signal estimation. The presence of fat has been successfully addressed through the use of $R_2^*$ mapping combined with chemical shift encoded water-fat separation methods that use multipeak spectral modeling of fat. When complex fitting is used, the bias in $R_2^*$ estimates caused by non-zero noise at low signal levels are naturally avoided. Also, the use of weighted least squares fitting or non-linear least squares fitting performed part of the chemical shift encoded decomposition can be used to avoid bias at high $R_2^*$ values. Finally, the augmentation in the signal decay and overestimation in $R_2^*$ values that results from macroscopic magnetic field inhomogeneities has also be addressed. Correction for this effect can be performed by measuring the local gradient of the local field inhomogeneity map ("field map"). The field map is estimated as part of complex chemical shift encoded water-fat separation methods. Hernando D, Vigen K K, Shimakawa A, Reeder S B. R2* mapping in the presence of macroscopic B0 field variations. Magn Reson Med. 2012 September; 68(3):830-40. recently demonstrated that the additional signal decay that results from gradients in the field map can be removed, avoiding overestimation of $R_2^*$. Finally, there is a known dependence on magnetic field strength on $R_2$ and $R_2^*$, which means that all $R_2$ and $R_2^*$ methods require calibration for different magnetic field strengths.

Despite the potential for both $R_2$ and $R_2^*$ based methods to quantify tissue iron concentration and the demonstration of a monotonic relationships between these parameters and tissue iron concentration, they both share a fundamental limitation. Specifically, the relationship between both $R_2$ and $R_2^*$, and HIC is not well understood. For this reason, the use of both $R_2$ and $R_2^*$ to measure iron concentration requires measurement of empirical calibration curves. While this approach is often practical in many circumstances, it is fundamentally limiting, since the development of new methods may require repeated recalibration, which is expensive and often prohibitive.

Therefore, it would be desirable to have a system and method for measuring or quantifying iron or other substances in a subject that is accurate and repeatable without the need for special calibrations, such as a calibration curve specific to each system or the like.

SUMMARY OF THE INVENTION

The present invention overcomes the aforementioned drawbacks by providing a system and method for assessing iron overload or gadolinium concentration in tissue by using magnetic susceptibility of tissue as a biomarker for measuring iron and other concentrations in tissue. As such a system and method for the quantification and assessment of iron and other substances in tissue is provided that does not require calibration curves and the like.

In accordance with one aspect of the present invention, a method is provided for assessing magnetic susceptibility of tissue of a subject within a region of interest (ROI) using a magnetic resonance imaging (MRI) system or a superconducting quantum interference device (SQUID). The method includes acquiring, with the MRI system or the SQUID, chemical-shift-encoded, water-fat separated data from the ROI and, from the water-fat separated data, determining a magnetic field inhomogeneity map across the ROI. The method also includes using the magnetic field inhomogeneity map, estimating a magnetic susceptibility of the tissue within the ROI.

In accordance with another aspect of the present invention, a magnetic resonance imaging (MRI) system is disclosed that includes a magnet system configured to generate a polarizing magnetic field about at least a portion of a subject arranged in the MRI system. The MRI system also includes a plurality of gradient coils configured to apply a gradient field to the polarizing magnetic field and a radio frequency (RF) system configured to apply an excitation field to the subject and acquire MR image data from a ROI. The MRI system further includes a computer system programmed to control the plurality of gradient coils and RF system to acquire chemical-shift-encoded, water-fat separated data from the ROI and determine, from the water-fat separated data, a magnetic field inhomogeneity map of the MRI system across the ROI. The computer system is further programmed to estimate, using the magnetic field inhomogeneity map, a magnetic susceptibility of the tissue within the ROI and determine at least one of a concentration of iron and a change in concentration of iron within the ROI using the magnetic susceptibility of the tissue within the ROI.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
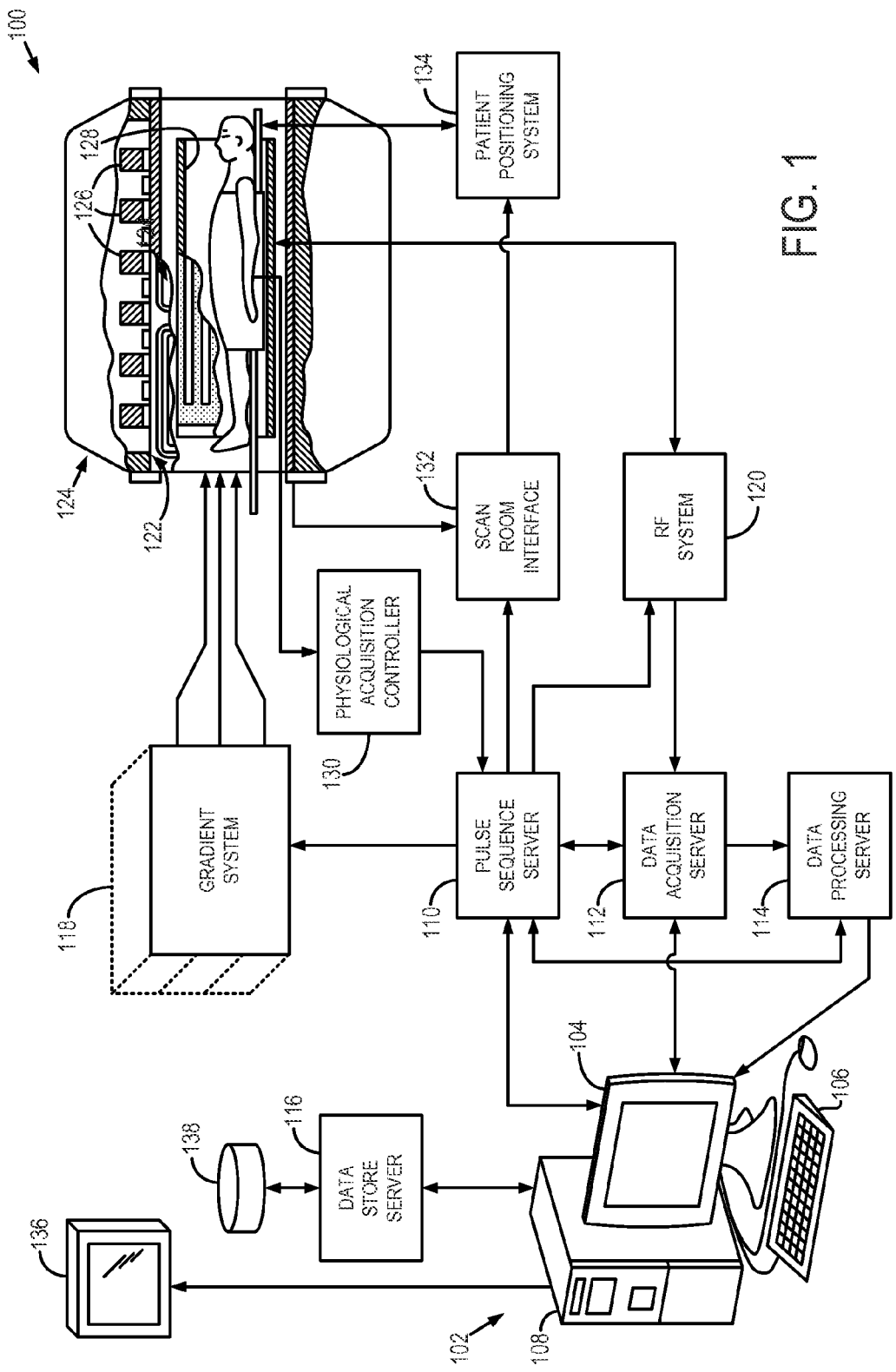
FIG. 1 is a block diagram of an exemplary magnetic resonance imaging (MRI) system that employs the present invention.

Referring now to FIG. 1, an exemplary MRI system 100 for use when practicing embodiments of the provided method is illustrated. The MRI system 100 includes a workstation 102 having a display 104, a keyboard 106, and computer 108. The workstation 102 provides the operator interface that enables scan prescriptions to be entered into the MRI system 100. The workstation 102 may be coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive M R signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components $M = \sqrt{I^2 + Q^2}$ and the phase of the received MR signal may also be determined $$\varphi = \tan^{-1}\left(\frac{Q}{I}\right).$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images. Of course, such processing may also be performed on other computer systems that are connected to a network or systems connected to the MRI system 100, such as system 136 described below, or more closely integrated with the MRI system 100.

Images reconstructed by the data processing server 114 are conveyed back to the workstation 102 where they are stored. Real-time images are stored in a data base memory cache (not shown in FIG. 1), from which they may be output to operator display 112 or a display or other connected computer system 136. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

The above-described MRI system 100 is capable of a variety of data acquisition and clinical procedures. For example, magnetic susceptibility of tissue is a fundamental property of tissue, and the relationship between tissue iron concentration and magnetic susceptibility is well understood. Methods, such as SQUID or MRI, that could accurately measure tissue susceptibility could be highly advantageous for measuring tissue iron concentration.

There are innumerable applications where direct measurement of tissue gadolinium concentration would be highly advantageous. These include first pass perfusion techniques that acquire a rapid set of images in a tissue of interest during the bolus injection of intravenous gadolinium based contrast agents (GBCA's). It is of great interest to measure absolute gadolinium concentration in order to perform parametric perfusion estimation and mapping. Most approaches rely on $T_1$ and $T_2^*$ weighted imaging. Unfortunately, the relationship between $T_1$ and $T_2^*$ weighed signal and gadolinium concentration is notoriously non-linear, and these methods are inherently semi-quantitative. Overall, the concentration of gadolinium that can be achieved in tissue during a first pass perfusion experiment using conventional extracellular agents is relatively low, and it is not certain whether significant changes in tissue magnetic susceptibility are detectable.

However, new, liver-specific contrast agents such as gadoxetic acid and, to a lesser extent, gadobenate dimeglumine, are taken up rapidly into hepatocytes and accumulate there in very high concentrations. It has recently been shown that relatively large changes in the $R2^*$ of liver can occur after the injection of gadoxetic acid. Methods that can measure magnetic susceptibility of tissue have the potential to measure tissue gadolinium concentration.

This may be of great importance in patients with liver disease. It is widely recognized that decreased uptake of liver specific contrast agents, such as gadoxetic acid into hepatocytes occurs in patients with reduced liver function, and that this agent has potential to measure liver function. Most approaches have focused on the use of $T_1$ weighted imaging, where large signal changes can be seen. However, these methods are unable to measure tissue gadolinium concentration for two reasons. First, the relationship between $T_1$ weighted signal intensity and gadolinium concentration is non-linear. Second, the relaxivity (constant of proportionality linking changes in $T_1$ with gadolinium concentration) inside hepatocytes is unknown. Although the first limitation could, in principle be addressed by $T_1$ mapping techniques, the second limitation may be difficult to surmount. For this reason, a fundamental biomarker, such as magnetic susceptibility of tissue that could measure gadolinium concentration directly would be of tremendous value in developing imaging methods to assess, for example, liver function. In fact, such methods, in combination with $T_1$ mapping methods, could be used to measure the relaxivity of liver specific gadolinium based contrast agents.

Magnetic Susceptibility

By definition, a material with volume susceptibility $\chi^V$ (unit-less, supersript "V" denotes volume susceptibility), can induce additional magnetic field, $B_{o,in}$, when placed in an external magnetic field B0. That is, the relationship is:

$$B_{o,in} = \chi^V B_o \quad \text{Eqn. (1).}$$

Further, since the susceptibility of a material depends on the concentration of the material, the induced magnetic field can be written as:

$$B_{o,in} = \chi^M [T] B_o \quad \text{Eqn. (2);}$$

where $\chi^M$ is the molar susceptibility (superscript "M" denotes molar, units=m³/mol or ml/mol) of substance T, and [T] is the concentration of substance T (units=mol/m³ or mol/ml). Note that molar susceptibility is related to volume susceptibility using the molecular weight (MW, units=g/mol or kg/mol) and density (units=g/ml or kg/m³) as:

$$\chi^M = \chi^V MW/\rho \quad \text{Eqn. (3).}$$

Alternatively, the mass susceptibility, $\chi^g$ (units=m³/kg or ml/g) can be used, and is related to volume susceptibility as:

$$\chi^g = \chi^V/\rho \quad \text{Eqn. (4).}$$

The change in magnetic field will be a linear combination of the contribution from all substances in the tissue. For example, in liver containing various concentrations (denoted by [-]) of iron (Fe), water (W), fat (F), and non-iron MR invisible material (I) the observed susceptibility would be the weighted sum of the component susceptibilities, such as:

$$\chi_{obs}^V = \chi_W^M[W] + \chi_F^V[F] + \chi_I^M[I] + \chi_{Fe}^M[Fe] \quad \text{Eqn. (5).}$$

Note that, although only water and fat actually produce MR signal, all substances present in the tissue can impact the magnetic susceptibility.

Using chemical shift encoded imaging, the proton density fat-fraction and proton density water fractions can be measured as:

$$\eta_F^{PDFF} = \frac{[F]}{[F]+[W]}, \eta_W^{PDFF} = \frac{[W]}{[F]+[W]}. \quad \text{Eqn. (6)}$$

If the fraction of MR invisible material is known (for example, approximately 39% in liver based on some studies), then it's possible to determine the volume fraction of water, fat, and MR invisible material, as:

$$\eta_F^V = \frac{[F]}{[F]+[W]+[I]}, \eta_W^V = \frac{[W]}{[F]+[W]+[I]}, \quad \text{Eqn. (7)}$$

$$\eta_I^V = \frac{[I]}{[F]+[W]+[I]}.$$

The conversion between proton-density-fat-fraction (PDFF) and volume fraction, based on known quantities of MR invisible species has been established. Using these conversions, and the expressions in equation 7, equation 5 can be rewritten as:

$$\chi_{obs}^V = \chi_W^V \eta_W^V + \chi_F^V \eta_F^V + \chi_I^V \eta_I^V + \chi_{Fe}^M[Fe] \quad \text{Eqn. (8).}$$

If the volume susceptibility, as well as volumetric water and fat fractions, can be measured, all from chemical shift based imaging, the concentration of iron can be derived as:

$$[Fe] = \frac{\chi_{obs}^V - (\chi_W^V \eta_W^V + \chi_F^V \eta_F^V + \chi_I^V \eta_I^V)}{\chi_{Fe}^M}. \quad \text{Eqn. (9)}$$

Note that this assumes that the fraction of MR invisible material is known/assumed. Also it assumes that the susceptibility of water, fat, and the MR invisible material are similar to water. Then, equation 9 can be approximated as:

$$[Fe] \approx \frac{\chi_{obs}^V - \chi_W^V}{\chi_{Fe}^W}. \quad \text{Eqn. (10)}$$

For applications aimed at measuring the concentration of gadolinium in tissue (for example, measuring gadoxetic acid concentration in liver as a biomarker of liver function), at least 2 time measurements of tissue susceptibility may be performed. In this situation, the concentration of gadolinium ([Gd]) can be determined by measuring the difference of the post-contrast and pre-contrast susceptibility, knowing the molar susceptibility of gadolinium ($\chi^{Gd}$), such as:

$$\Delta\chi_{obs}^V = \chi_{post}^V - \chi_{pre}^V = \chi_{Gd}^M[Gd] \quad \text{Eqn. (11).}$$

In this case, it may not be desirable to perform any baseline corrections (see below), assuming the baseline offset does not change between pre- and post-contrast acquisition. This approach may also be advantageous to measuring the concentration of iron oxide after the administration of iron oxide agents such as Ferridex.

Measurement of the Field Inhomogeneity Map ("Field Map")

There are many ways to measure the magnetic field inhomogeneity or produce a "field map." A particularly useful method to measure the field map, particularly in the presence of fat, is the use of chemical shift encoded water-fat separation methods. The signal acquired as a multi-echo gradient echo acquisition, measured at echo time $t_n$ from a voxel containing water (W) and fat (F) can be written as:

$$s(t_n) = \left(W + F\sum_{p=1}^{P} r_p e^{i2\pi f_p t_n}\right) e^{-R_2^* t_n} e^{i2\pi \psi t_n}; \quad \text{Eqn. (12)}$$

where $R_2^*$ is the rate of transverse magnetization decay, and the multipeak modeling of fat peaks is characterized by the sum of complex exponential with P peaks with frequency $f_p$ and relative amplitudes $r_p$ such that $$\sum_{p=1}^{P} r_p = 1.$$

Importantly, the term ψ (units=Hz) and is directly related to the magnetic field inhomogeneity by the gyromagnetic ratio, such as:

$$\psi(r) = \frac{\gamma}{2\pi} B_{o,in}(r);  \qquad \text{Eqn. (13)}$$

where $$\frac{\gamma}{2\pi} = 42.58 \text{ MHz/T}.$$

For practical purposes, the term "field map" is used interchangeably for ψ(r) (Hz) and $B_{o,in}$ (r) (Tesla).

Relationship Between Field Map and Susceptibility

As mentioned above, there is a very strong influence of an object's shape on the observed magnetic field inhomogeneity. These expressions are mathematically complex, and can be written as follows:

$$B_{o,in}(r) = |B_0| \cdot \int_{r'} \chi(r') \cdot d_z(r - r') dr'; \qquad \text{Eqn. (14)}$$

$$d_z(r) = \frac{3\cos^2\theta - 1}{4\pi \cdot |r|^3}; \qquad \text{Eqn. (15)}$$

where $B_{o,in}$ (r) is the z-component of the perturbation of the magnetic field due to the susceptibility χ(r), $d_z$(r) is the z-component of the spatial unit dipole, θ is the angle between $B_0$ and r, r is the 3D position vector. The z-component of the magnetic field inhomogeneity is related to the susceptibility of an object in Fourier space, as follows:

$$B_{o,in}(k) = B_o\left(\frac{1}{3} - \frac{k_z^2}{k_x^2 + k_y^2 + k_z^2}\right)\chi(k); \qquad \text{Eqn. (16)}$$

where the Fourier transform (k-space representation) of the magnetic field inhomogeneity, $B_{o,in}$(k) is directly related to the Fourier representation of the susceptibility map, χ(k), through a constant (⅓), and a filter function $$\frac{k_z^2}{k_x^2 + k_y^2 + k_z^2}.$$

Figure 2:
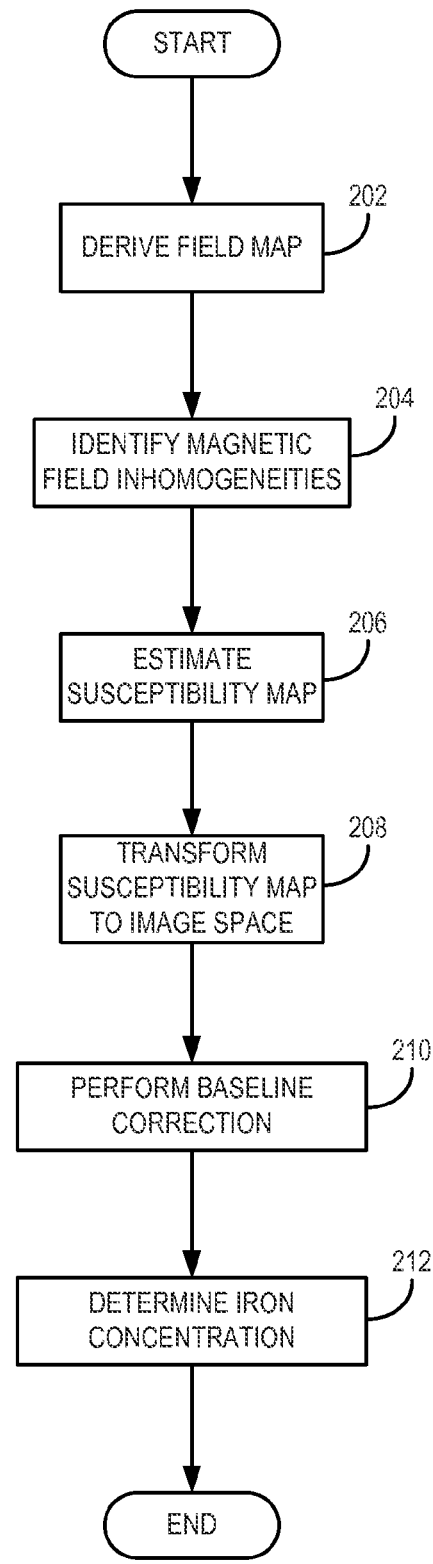
FIG. 2 is a flow chart setting forth steps of a process for assessing tissue in accordance with the present invention.

Referring to FIG. 2, an exemplary processing for solving for the susceptibility map, χ(r), begins at process block 202 by deriving a field map, $$\psi(r) = \frac{\gamma}{2\pi} B_{o,in}(r),$$

to, thereby, measure $B_{o,in}$ (r) in image space. At process block 204, the process continues by performing Fourier transform of $B_{o,in}$ (r) to obtain $B_{o,in}$ (k). At process block 206, a dipole inversion of equation 16 is performed to obtain $\hat{\chi}$(k), an estimate of χ(k). The dipole inversion has been described by, for example, Liu C, Li W, Johnson G A, Wu B. High-field (9.4 T) MRI of brain dysmyelination by quantitative mapping of magnetic susceptibility. NeuroImage 2011; 56(3):930-938; Li W, Wu B, Liu C. Quantitative susceptibility mapping of human brain reflects spatial variation in tissue composition. NeuroImage 2011; 55(4):1645-1656; Liu T, Spincemaille P, de Rochefort L, Wong R, Prince M, Wang Y. Unambiguous identification of superparamagnetic iron oxide particles through quantitative susceptibility mapping of the nonlinear response to magnetic fields. Magnetic resonance imaging 2010; 28(9):1383-1389; andde Rochefort L, Brown R, Prince M R, Wang Y. Quantitative M R susceptibility mapping using piece-wise constant regularized inversion of the magnetic field. Magnetic resonance in medicine: official journal of the Society of Magnetic Resonance in Medicine/Society of Magnetic Resonance in Medicine 2008; 60(4):1003-1009, each of which is incorporated herein by reference. Unfortunately, despite these efforts, the dipole inversion presents a challenging problem, largely related to the fact that the k-space filter in equation 16 is singular at the origin of k-space (k=0), and is also zero at all points in the ($k_x$, $k_y$, $k_z$) space where $k_z^2$=⅓*($k_x^2$+$k_y^2$+$k_z^2$). Mathematical inversion of equation 16 to determine χ(k) can be achieved, for example, using constrained reconstruction approaches, such as regularization and other methods to avoid instability. Many choices of inversion method are possible and within the scope of the present invention.

Continuing with respect to FIG. 2, an inverse Fourier transform of $\hat{\chi}$(k) is performed at process block 208 to obtain $\hat{\chi}$(r), an estimate of χ(r), the susceptibility map, in image space. At process block 210, a baseline correction is performed using a baseline reference standard It is noted that χ(k) cannot be solved at k=0. That is, the DC component of χ(k) cannot be determined. This implies that after performing the inverse Fourier transform above that χ(r) will have an unknown global constant offset. For this reason, it is desirable to perform a baseline correction using a reference object, such as adipose tissue, fluid within the stomach or an external phantom reference. The reference object (or tissue) should have known susceptibility in order to determine the constant offset needed to allow calculation of the absolute susceptibility in the tissue of interest.

Under the assumption that key substances with susceptibility greatly different than water and fat, such as iron and gadolinium do not accumulate in significant quantify in adipose tissue, adipose tissue may serve as an excellent baseline reference tissue for susceptibility measurements. As will be further detailed below, after injection of gadolinium contrast, any tissue that accumulates significant quantities of gadolinium (such as gadoxetic acid in the liver) may not be a suitable reference tissue. Alternatively, any tissue where the susceptibility is known with certainty could be used as a baseline reference. Another example would be fluid within the stomach (for example, the patient could be asked to ingest a known fluid such as water prior to the exam, to be used as a reference substance), or an MRI visible reference standard (such as a phantom) may be included in the field of view. Tissues such as liver, pancreas, myocardium, spleen, bone marrow, and muscle, among others, can have varying concentrations of iron and, in general, may not be suitable as a baseline reference unless the quantity of iron were known or a reasonable assumption could be made.

In any case, at process block 212, the concentration of iron (Fe) can be determined using equation 9 or 10 above.

Notably, the estimated absolute tissue susceptibility can be used to determine the tissue concentration of pre-existing iron overload in tissue. Since iron is the only non-trace substance with high susceptibility to accumulate in tissue, measurement of absolute tissue susceptibility can be used to allow direct measurement of iron concentration.

Figure 3:
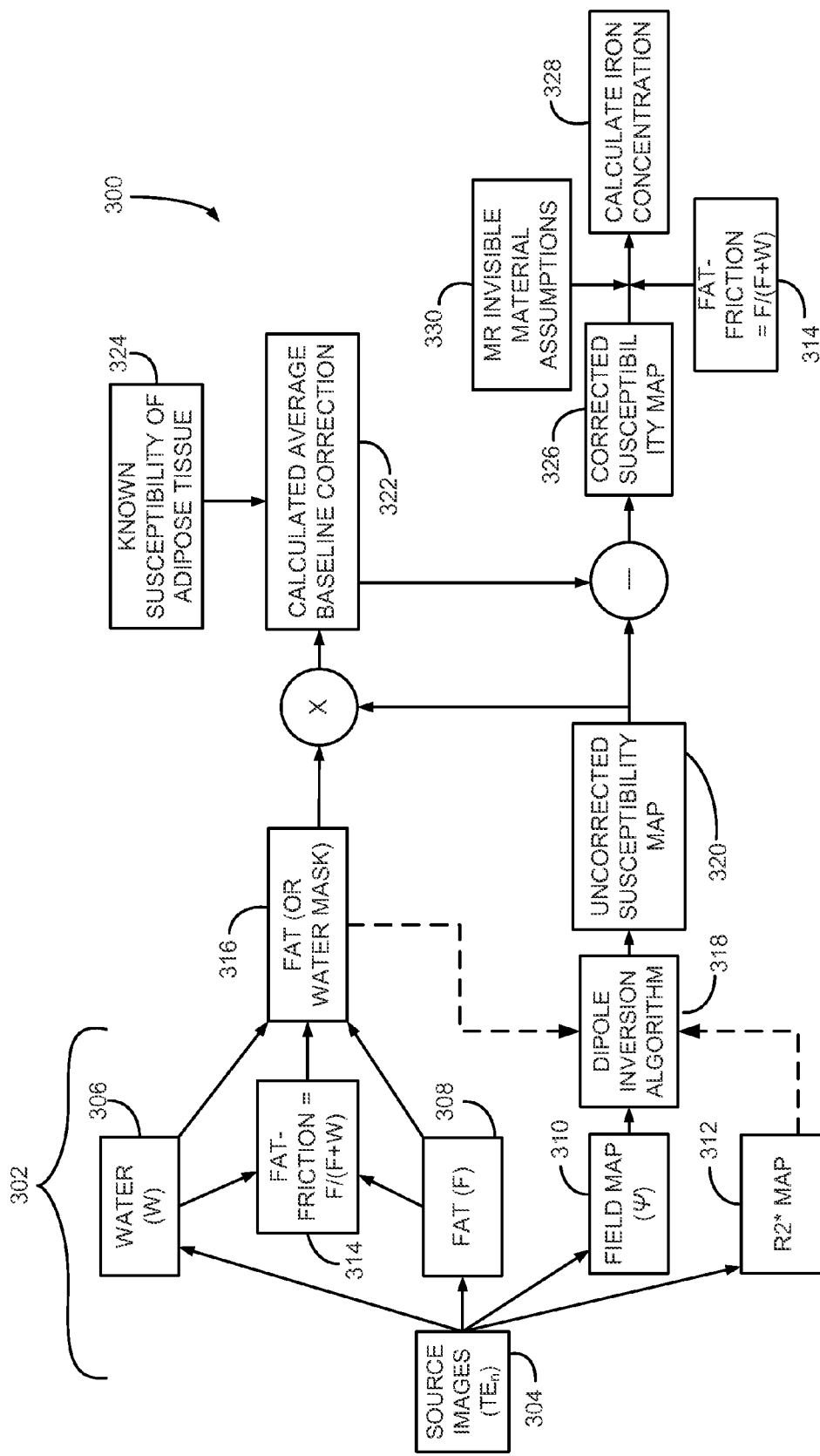
FIG. 3 is a schematic flow diagram of an algorithm in accordance with the present invention.

Referring to FIG. 3, the present invention can be implemented within a process 3000, such as follows. First, a complex chemical shift encoded water-fat separation algorithm 302, such as IDEAL or VARPRO may be performed to derive source images 304 that can be decomposed into a water image 306, a fat image 308, a field map 310, and an R2* map 312.

If the presence of fat in tissue is to be used in the complete calculation of iron concentration in equation 9, care should be taken to ensure that the water and fat addresses all confounding factors include spectral modeling of fat (such as described in Yu H, Shimakawa A, McKenzie C A, Brodsky E, Brittain J H, Reeder S B. Multiecho water-fat separation and simultaneous R2* estimation with multifrequency fat spectrum modeling. Magnetic resonance in medicine: official journal of the Society of Magnetic Resonance in Medicine/Society of Magnetic Resonance in Medicine 2008; 60(5):1122-1134, which is incorporated herein by reference), R2* correction (Yu H, McKenzie C A, Shimakawa A, Vu A T, Brau A C, Beatty P J, Pineda A R, Brittain J H, Reeder S B. Multiecho reconstruction for simultaneous water-fat decomposition and $T_2^*$ estimation. Journal of magnetic resonance imaging: JMRI 2007; 26(4): 1153-1161 and Yu H, Shimakawa A, McKenzie C A, Brodsky E, Brittain J H, Reeder S B. Multiecho water-fat separation and simultaneous R2* estimation with multifrequency fat spectrum modeling. Magnetic resonance in medicine: official journal of the Society of Magnetic Resonance in Medicine/Society of Magnetic Resonance in Medicine 2008; 60(5):1122-1134, which are incorporated herein by reference), $T_1$ related bias (Liu C Y, McKenzie C A, Yu H, Brittain J H, Reeder S B. Fat quantification with IDEAL gradient echo imaging: correction of bias from T(1) and noise. Magnetic resonance in medicine: official journal of the Society of Magnetic Resonance in Medicine/Society of Magnetic Resonance in Medicine 2007; 58(2):354-364, which is incorporated herein by reference), noise related bias (Id.), and eddy current correction (Yu H, Shimakawa A, Hines C D, McKenzie C A, Hamilton G, Sirlin C B, Brittain J H, Reeder S B. Combination of complex-based and magnitude-based multiecho water-fat separation for accurate quantification of fat-fraction. Magnetic resonance in medicine: official journal of the Society of Magnetic Resonance in Medicine/Society of Magnetic Resonance in Medicine 2011; 66(1):199-206 and Hernando D, Hines C D, Yu H, Reeder S B. Addressing phase errors in fat-water imaging using a mixed magnitude/complex fitting method. Magnetic resonance in medicine: official journal of the Society of Magnetic Resonance in Medicine/Society of Magnetic Resonance in Medicine 2012; 67(3):638-644, which are incorporated herein by reference).

From the separated water and fat signals 306, 308, a fat fraction map 314 and fat-fraction mask 316 (or water fraction mask) can be calculated. The water and fat signals 306, 308, along with the fat-fraction or water-fraction images can be used to calculate a fat mask through thresholding methods that mask out background noise and identify adipose tissue that contain mostly fat, such as described in Poonawalla A H, Sjoberg B P, Rehm J L, Hernando D, Schroeder M E, Hines C D, Irarrazaval P, Reeder S B. Adipose Tissue MRI for Quantitative Measurement of Central Obesity. Journal of Magnetic Resonance Imaging 2012; In press, which is incorporated herein by reference.

As indicated, such a fat-mask 316 can be used as an optional constraint in a dipole inversion step 318, by enforcing that the calculated susceptibility is constant throughout the adipose tissue. Effectively, this process helps to remove any slowly varying magnetic field inhomogeneities, such as those related to poor background shimming. Given that there is typically a large amount of adipose tissue distributed widely in the body, adipose tissue makes a natural and advantageous constraint for this purpose. Note that the R2* 312 map may also be a useful constraint in the dipole inversion 318.

The result of the dipole inversion 318 is an uncorrected susceptibility map 320. The uncorrected susceptibility map can be reconstructed using an established or modified reconstruction. The uncorrected susceptibility map 320 will have an unknown global constant shift that should be subsequently removed. This offset may be calculated, for example, by multiplying the fat mask 314 and the uncorrected susceptibility map 320. An average uncorrected susceptibility in adipose tissue 322 can be calculated from the resulting map. Using known values of the molar susceptibility in adipose tissue as the baseline reference value 324, a baseline correction constant (a scalar) can be calculated and subtracted from the uncorrected susceptibility map 320 to generate a corrected susceptibility map 326. Note that the value of the susceptibility in adipose tissue can be determined a priori from published values in the literature, or as a linear combination of the known values of the susceptibility of water and fat, using the measured concentration of water and fat determined from the chemical shift water-fat decomposition.

Using the corrected susceptibility map 326, an iron concentration 328 can be calculated (either from regions of interest or as a map) using equation 9 above. If there is a significant percentage of fat in the tissue, the fat-fraction map 314 can be used to determine the relative contributions of fat, water. When combined with information regarding MR invisible material 330 the relative contribution of MR invisible material can also be considered. If the contributions from fat and MR invisible material can be ignored, or if the susceptibility of water, fat, and MR invisible material can be assumed to be similar, then equation 10 can be used to calculate the concentration of iron 328.

Figure 4:
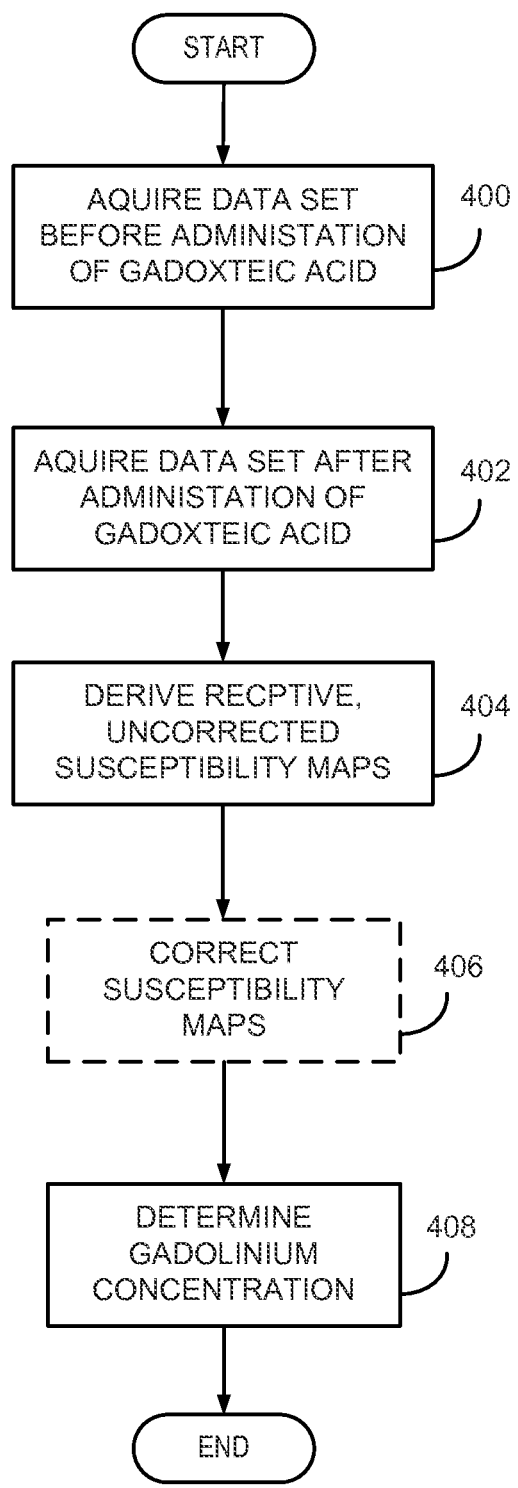
FIG. 4 is a flow chart setting forth steps of a process for assessing changes in the magnetic susceptibility of tissue in accordance with the present invention

Referring to FIG. 4, the above-described processes can be used to achieve the goal of calculating the concentration of gadolinium (for example, gadoxetic acid) using two separate data sets. At process block 400 a first data set is acquired before administration of gadoxetic acid and at process block 402 a second data set is acquired after the administration of gadoxetic acid. Using these two data sets, the above-described process is performed to derive respective, uncorrected susceptibility maps at process block 404. In principle, the difference between two uncorrected susceptibility maps should be sufficient to calculate the concentration of gadolinium. If there is reason to believe that the baseline correction factor has changed, then at process block 406, complete, corrected susceptibility maps can optionally be calculated and, at process block 408, the difference used to determine gadolinium concentration, such as by ay of equation 11 above.

Note that calculation of iron concentration and gadolinium uptake using this approach are not mutually exclusive. However, if looking to achieve both determinations simultaneously, only the pre-contrast images should be used to measure iron concentration, since the presence of gadolinium would confound the ability to measure iron overload.

Thus, measurement of the change in tissue susceptibility can be used to determine the concentration of a substance introduced into tissue, such as injected gadolinium based contrast agents (GBCA's) or injected iron oxide agents. The accumulated concentration of certain GBCA's such as gadoxetic acid or gadobenate dimeglumine after a delay (for example, 20 minutes for gadoxetic acid) may reflect hepatic function. Measurement of gadolinium concentration provides direct measurement of this potentially important biomarker of liver function.

In this situation, measurement of the relative (or absolute) susceptibility before and after the injection of gadolinium or iron oxides could be used to determine the concentration of gadolinium in tissue. This assumes that the concentration of gadolinium prior to injection is zero (which is a good assumption unless the patient had a very recent injection).

Other potential applications include the measurement of gadolinium tissue concentration during the first pass of contrast as part of a perfusion related imaging procedures. Current methods rely on T1 and T2* based methods, which are limited by the non-linear relationship between T1 and T2* weighted signal and gadolinium concentration.

An approximate "step-off" method may also be used as a way to measure iron concentration in the liver. Specifically, if the body can be approximated as a cylinder or a very long object, or if the interface between the liver and the adjacent adipose tissue is parallel to the main magnetic field (such as in the lateral aspect of the right lobe of the liver), then the difference in field map between two adjacent tissues can be used to determine the iron concentration. Specifically, in this particularly geometric configuration/approximation, dipole inversion may not be needed.

Using fat (or other appropriate tissue or other reference) as a baseline is advantageous, not only for "step-off" approaches, to measure susceptibility in tissue, but also for comprehensive quantitative susceptibility mapping techniques that use dipole inversion methods. Methods that estimate susceptibility from field maps benefit from a baseline reference to determine the absolute susceptibility.

Figure 5:
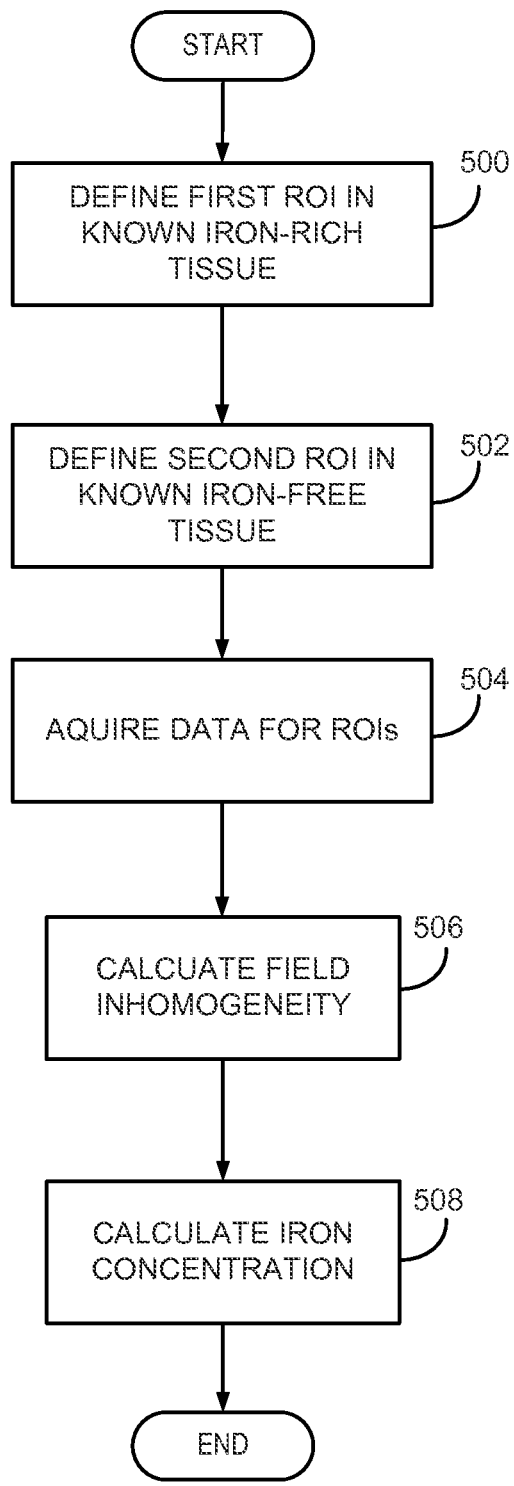
FIG. 5 is a flow chart setting forth steps of a process for assessing tissue in accordance with the present invention.

Referring to FIG. 5, at process block 500, a first region of interest (ROI) is placed in a known iron-rich area, such as the inferior portion of the liver, for example, far from regions of magnetic field inhomogeneity. At process block 502, a second ROI is placed in the adjacent adipose tissue. At process block 504, data sets is acquired from each of the ROIs and, at process block 506, using the above-described techniques, a measure of the field inhomogeneity is calculated as a difference between an iron containing liver and iron-free (or low iron) adipose tissue and, at process block 508.

The susceptibility difference between two adjacent tissues ($\Delta\chi$) is related to the difference in magnetic field ($\Delta B_0$) at both sides of the boundary, based on the boundary conditions for Maxwell's equations. Including the sphere of Lorentz effects and hyperfine shift the susceptibility difference and magnetic field difference can be written:

$$\Delta\chi = \frac{3\Delta B_0}{1-\cos^2\theta + S_{hf}}; \qquad \text{Eqn. 17}$$

where $\Delta B_0$ is the magnetic field difference in ppm, $\theta$ is the angle between the vector perpendicular to the boundary and the main $B_0$ field, and $S_{hf}$ is the hyperfine shift assumed to be −0.133. In this work, boundaries parallel to the main magnetic field were selected such that $\theta \approx 90°$ (and thus $\cos\theta \approx 0$), by measuring $B_0$ fields in the lateral aspect of the right lobe of the liver. With this constraint, Eqn. 17 can be simplified as:

$$\Delta\chi = 3.46\Delta B_0 \qquad \text{Eqn 18.}$$

In the case of focusing on susceptibility differences between liver tissue and nearby subcutaneous fat tissue, even if subcutaneous fat and liver are not in direct contact, the subcutaneous fat can be used as a reference for susceptibility measurements due to the fact that the distance to the liver is usually small. In addition, subcutaneous fat can be assumed to be homogeneous with no significant iron accumulation since it is not part of the reticuloendothelial system (RES) that accumulates iron tissue in Kupffer cells and other phagocytic white blood cells.

In this setting, the susceptibility difference between liver and subcutaneous fat can be decomposed into two components, as follows:

$$\Delta\chi = \Delta\chi_{base} + \Delta\chi_{Fe} \qquad \text{Eqn. 19;}$$

where $\Delta\chi_{base}$ is the baseline susceptibility difference between both tissues (in the absence of liver iron), and $\Delta\chi_{Fe}$ is the additional paramagnetic contribution of iron to the susceptibility of liver. Equation 19 is an approximation, by assuming that iron is the only factor affecting the magnetic susceptibility of liver tissue. For instance, it ignores the potential presence of liver fat. The presence of liver fat could be included by introducing an additional term $\Delta X_{fat} = \eta_{fat} X_{fat}$ in Eqn. 19, consistent of the relative concentration of fat and its susceptibility.

Based on the paramagnetic properties of storage iron, the paramagnetic contribution of iron to susceptibility can be described as:

$$\Delta\chi_{Fe} = \frac{N\mu_0\mu_{eff}^2\mu_B^2}{3kT}; \qquad \text{Eqn. 20}$$

where N is the number of iron particles per m$^3$, $\mu_0 = 4\pi \times 10^{-7}$ V·s/(A·m) is the vacuum permeability, $\mu_{eff}$ is the effective number of Bohr magnetons per atom, approximately = 3.78, $\mu_B = 9.274 \times 10^{-24}$ is the Bohr magneton, $k = 1.38 \times 10^{-23}$ J·K$^{-1}$ is the Boltzmann constant, and T≈310 K is body temperature. Based on Eqn. 20, and using the approximated density 1.05 g/cm$^3$ for liver tissue, the iron concentration (in g Fe/g wet tissue) can be related to the paramagnetic contribution of iron to the susceptibility, as follows:

$$[Fe]_{wet} = 0.74\Delta\chi_{Fe} = 0.74(\Delta\chi - \Delta\chi_{base}) \qquad \text{Eqn. 21.}$$

Finally, combining Eqns. 18 and 20, the iron concentration can be expressed in terms of the measured magnetic field difference $\Delta B_0$ as follows:

$$[Fe]_{wet} = 2.56\Delta B_0 - 0.74\Delta\chi_{base} \qquad \text{Eqn. 22.}$$

Note that liver iron concentration is typically expressed in mg Fe/g dry tissue. That is, it is typically expressed as $[Fe]_{dry}$ instead of $[Fe]_{wet}$. The relationship between these two measures of iron concentration is not completely understood. Recent works have suggested a conversion factor of 5.5+/−1.0. Using the conversion factor $[Fe]_{dry} = 5.5[Fe]_{wet}$, the final expression for iron concentration in mg Fe/g dry tissue can be represented as follows:

$$[Fe]_{dry} = 14.08\Delta B_0 - 4.07\Delta\chi_{base} \qquad \text{Eqn. 23.}$$

In this work, the baseline susceptibility difference $\Delta\chi_{base}$ is calibrated from a set of control subjects, e.g., by assigning them an average $[Fe]_{dry}=1.0$ mg Fe/g dry tissue, which is near the center of the range of normal concentration of liver iron in healthy subjects. Aside from this baseline, this approach requires no calibration, in contrast with R2- or R2*-based iron quantification techniques.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for assessing magnetic susceptibility of tissue of a subject within a region of interest (ROI) using a magnetic resonance imaging (MRI) system, the method comprising the steps of:
    a) acquiring, with the MRI system, chemical-shift-encoded, water-fat separated data from the ROI;
    b) from the water-fat separated data, determining with a computer system, a magnetic field inhomogeneity map across the ROI;
    c) using the magnetic field inhomogeneity map, estimating with the computer system, a magnetic susceptibility of the tissue within the ROI;
    d) correcting, with the computer system, the estimated magnetic susceptibility of the tissue within the ROI for background effects and using a baseline susceptibility of known susceptibility to determine an offset that provides an absolute susceptibility; and
    e) using the corrected susceptibility map providing absolute susceptibility within the ROI and at least one of assumptions about magnetic resonance invisible materials or a fat fraction of the ROI, generating an iron concentration map.

2. The method of claim 1 wherein the tissue is a first tissue, the ROI is a first ROI positioned in the first tissue, and the method further includes:
    a)i) acquiring, with the MRI system, chemical-shift-encoded, water-fat separated data from a second ROI positioned in a second tissue that is adjacent the first tissue;
    b)i) from the water-fat separated data, determining with the computer system, another magnetic field inhomogeneity map across the second ROI;
    c)i) using the another magnetic field inhomogeneity map, estimating with the computer system, a magnetic susceptibility of the second tissue within the second ROI; and
    e) determining with the computer system, a susceptibility difference between the first ROI and the second ROI.

3. The method of claim 2 wherein the first ROI is located proximate to the second ROI.

4. The method of claim 2 wherein the first tissue includes liver tissue and the second tissue includes subcutaneous adipose tissue.

5. The method as recited in claim 2, wherein step d) includes correcting the estimated magnetic susceptibility of the first tissue within the first ROI by selecting with the computer system a baseline susceptibility value that is based on known susceptibility values and subtracting the baseline susceptibility value from the estimated magnetic susceptibility of the first tissue within the first ROI.

6. The method of claim 1 wherein steps a) through d) are performed at a first time before being repeated at a second time and wherein the method further includes:

e) determining with the computer system, a susceptibility difference between the ROI at the first time and the ROI at the second time.

7. The method of claim 6 further comprising injecting the subject with a contrast agent and wherein steps a) through d) are performed at the first time before injection of the contrast agent and steps a) through d) are performed at the second time after injection of the contrast agent.

8. The method of claim 7 wherein step e) includes determining with the computer system, a susceptibility difference between the ROI at the first time and the ROI at the second time caused by the injection of the contrast agent.

9. The method of claim 7 wherein step c) includes performing a dipole inversion with the computer system to estimate the susceptibility as a relative susceptibility between tissues.

10. The method of claim 1 wherein step c) includes performing a dipole inversion with the computer system to estimate the susceptibility as a relative susceptibility between tissues.

11. The method of claim 10 wherein step b) further includes generating with the computer system, an R2* map and step c) includes using the R2* map as a computational constraint in the dipole inversion.

12. The method of claim 1 wherein step b) further includes generating with the computer system, an R2* map and step d) includes correcting the estimate of the magnetic susceptibility of the tissue using the R2* map in an empirical estimate of iron overload in the tissue as part of the baseline susceptibility determination.

13. The method of claim 1 wherein the baseline susceptibility of known susceptibility is derived from one of adipose tissue, fluid with the subject, or an external reference.

14. A magnetic resonance imaging (MRI) system comprising:
    a magnet system configured to generate a polarizing magnetic field about at least a portion of a subject arranged in the MRI system;
    a plurality of gradient coils configured to apply a gradient field to the polarizing magnetic field;
    a radio frequency (RF) system configured to apply an excitation field to the subject and acquire MR image data from a ROI;
    a computer system programmed to:
        control the plurality of gradient coils and RF system to acquire chemical-shift-encoded, water-fat separated data from the ROI;
        determine, from the water-fat separated data, a magnetic field inhomogeneity map of the MRI system across the ROI;
        estimate, using the magnetic field inhomogeneity map, a magnetic susceptibility of the tissue within the ROI;
        correct the estimated magnetic susceptibility of the tissue within the ROI for background effects and relative measure of magnetic susceptibility using at least a baseline susceptibility; and
        determine at least one of a concentration of iron and a change in concentration of iron within the ROI using the corrected estimate of the magnetic susceptibility of the tissue within the ROI and at least one of a fat fraction of the ROI or magnetic resonance invisible material assumptions.

15. The MRI system of claim 14 wherein the computer system is further programmed to perform a dipole inversion to estimate the magnetic susceptibility as a relative susceptibility between tissues.

16. The MRI system of claim 15 wherein the computer system is further programmed to generate an R2* map from the water-fat separated data and use the R2* map as a computational constraint in the dipole inversion.

17. The MRI system of claim 14 wherein the computer system is further programmed to:
control the gradient coils and RF system to acquire chemical-shift-encoded, water-fat separated data from another ROI separate from the ROI;
determine, from the water-fat separated data from the another ROI, another magnetic field inhomogeneity map of the MRI system across the another ROI;
estimate, using the another magnetic field inhomogeneity map, a magnetic susceptibility of the tissue within the another ROI; and
determine a susceptibility difference between the ROI and the another ROI.

18. The MRI system of claim 17 wherein the ROI is located proximate to the another ROI.

19. The MRI system of claim 14 wherein the computer system is further programmed to acquire data at a first time from the ROI before injection of a contrast agent and acquire data at a second time from the ROI after injection of the contrast agent.

20. The MRI system of claim 19 wherein the computer is further programmed to determine a susceptibility difference between the ROI at the first time and the ROI at the second time caused by the injection of the contrast agent.

* * * * *

UNITED STATES PATENT AND TRADEMARK OFFICE
CERTIFICATE OF CORRECTION

PATENT NO. : 9,943,246 B2  
APPLICATION NO. : 13/684000  
DATED : April 17, 2018  
INVENTOR(S) : Reeder et al.

Page 1 of 1

It is certified that error appears in the above-identified patent and that said Letters Patent is hereby corrected as shown below:

In the Claims

Column 16, Claim 14, Line 60, "measure" should be --measures--.

Signed and Sealed this
Twenty-sixth Day of June, 2018

Andrei Iancu
*Director of the United States Patent and Trademark Office*